(12) United States Patent
Kim et al.

(10) Patent No.: US 10,085,700 B2
(45) Date of Patent: *Oct. 2, 2018

(54) X-RAY DEVICE AND METHOD FOR CONTROLLING THE SAME

(71) Applicant: SAMSUNG ELECTRONICS CO., LTD., Suwon-si (KR)

(72) Inventors: Hyun Sun Kim, Hwaseong-si (KR); Jong Hyun Shin, Seoul (KR); Woo Sup Han, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/269,512

(22) Filed: May 5, 2014

(65) Prior Publication Data

US 2014/0301536 A1 Oct. 9, 2014
US 2016/0183894 A9 Jun. 30, 2016

Related U.S. Application Data

(63) Continuation of application No. 13/768,365, filed on Feb. 15, 2013, now Pat. No. 8,781,073.

(30) Foreign Application Priority Data

Feb. 15, 2012 (KR) .......................... 10-2012-0015545

(51) Int. Cl.
*A61B 6/00* (2006.01)

(52) U.S. Cl.
CPC ................ *A61B 6/46* (2013.01); *A61B 6/467* (2013.01); *A61B 6/54* (2013.01); *A61B 6/548* (2013.01)

(58) Field of Classification Search
CPC .. A61B 6/46; A61B 6/045; A61B 6/00; A61B 6/102; A61B 6/467; A61B 6/54;
(Continued)

(56) References Cited

U.S. PATENT DOCUMENTS 4,214,169 A 7/1980 Hotta et al.
4,773,086 A 9/1988 Fujita et al.
(Continued)

FOREIGN PATENT DOCUMENTS

CN 1573534 A 2/2005
CN 101652099 2/2010
(Continued)

OTHER PUBLICATIONS

PCT International Search Report mailed May 27, 2013 in corresponding International Application No. PCT/KR2013/001205.
(Continued)

*Primary Examiner* — Irakli Kiknadze
(74) *Attorney, Agent, or Firm* — Staas & Halsey LLP

(57) ABSTRACT

Disclosed are an X-ray device to inform a patient of X-ray irradiation through a sound and a method for controlling the same. The X-ray device includes an input portion to output a first-step press signal and a second-step press signal according to an operator input, a high-voltage generating portion to perform pre-heating, and to output a ready completion signal when the high-voltage generating portion completes pre-heating, a control portion to output a sound output signal when it receives both the second-step press signal output from the input portion and the ready completion signal output from the high-voltage generating portion, and a sound output portion to receive the sound output signal from the control portion and to output a predetermined sound.

14 Claims, 13 Drawing Sheets

(58) Field of Classification Search
CPC ..... A61B 6/548; A61B 8/0825; A61B 6/4417; A61B 6/502; A61B 5/0091; A61B 5/0095; A61B 5/4312; A61B 8/5238; A61B 6/0414; A61B 8/14; A61B 8/4416; A61B 2562/046; A61B 5/145; A61B 5/14532; A61B 5/14546; G01R 15/08; G01R 29/00
USPC .................................. 378/98, 101, 114, 117
See application file for complete search history.

(56) References Cited

U.S. PATENT DOCUMENTS

| | | | |
|---|---|---|---|
| 4,991,193 | A | 2/1991 | Cecil et al. |
| 5,206,894 | A | 4/1993 | Makrinos et al. |
| 5,444,756 | A | 8/1995 | Pai et al. |
| 5,692,027 | A * | 11/1997 | Yoshimura et al. ............ 378/38 |
| 7,403,594 | B2 | 7/2008 | Endo et al. |
| 8,781,073 | B2 * | 7/2014 | Kim et al. ...................... 378/98 |
| 2002/0050568 | A1 | 5/2002 | Nonaka |
| 2002/0088566 | A1 | 7/2002 | Doelle |
| 2003/0147490 | A1 | 8/2003 | Stabe et al. |
| 2005/0157177 | A1 * | 7/2005 | Fukushima ............ H04N 5/772 348/207.99 |
| 2005/0220269 | A1 * | 10/2005 | Endo et al. .................. 378/114 |
| 2006/0104412 | A1 * | 5/2006 | Kawanabe ............ A61B 6/032 378/20 |
| 2008/0075233 | A1 | 3/2008 | Coombs |
| 2009/0087099 | A1 * | 4/2009 | Nakamura .................... 382/190 |
| 2010/0166143 | A1 | 7/2010 | Sung et al. |
| 2011/0291800 | A1 * | 12/2011 | Butzine .................. A61B 6/544 340/8.1 |
| 2012/0128127 | A1 * | 5/2012 | Chicchetti ................. G01T 7/00 378/62 |
| 2012/0187312 | A1 | 7/2012 | Guez |

FOREIGN PATENT DOCUMENTS

| | | |
|---|---|---|
| CN | 101868181 | 10/2010 |
| CN | 102068267 | 5/2011 |
| EP | 0 923 275 A2 | 5/1999 |
| EP | 0923275 | 6/1999 |
| JP | 10099318 A * | 4/1998 |
| WO | 2008/120886 | 10/2008 |

OTHER PUBLICATIONS

Extended European Search Report issued Jul. 5, 2013 in corresponding European Application No. 13155509.6.

Office Action mailed Sep. 6, 2013 in corresponding U.S. Appl. No. 13/768,365.

Notice of Allowance mailed May 5, 2014 in corresponding U.S. Appl. No. 13/768,365.

U.S. Appl. No. 13/786,365, filed Feb. 15, 2013, Hyun Sun Kim, et al., Samsung Electronics Co., Ltd.

Chinese Office Action issued Apr. 13, 2015 in corresponding Chinese Patent Application 201380009760.2.

European Communication under Rule 71(3) EPC issued Mar. 6, 2015 in corresponding European Patent Application 13 155 509.6.

European Search Report dated Dec. 17, 2015 issued in corresponding European Patent Application 15176981.7-1660.

U.S. Appl. No. 13/768,365, dated Feb. 15, 2013, Hyun Sun Kim et al., Samsung Electronics Co., Ltd., Suwon-si, KR.

European Decision of Intention to grant dated Aug. 10, 2017 in corresponding European Patent Application No. 15176981.7.

* cited by examiner

X-RAY DEVICE AND METHOD FOR CONTROLLING THE SAME

CROSS-REFERENCE TO RELATED APPLICATION

This application is a continuation of U.S. Ser. No. 13/768,365, filed Feb. 15, 2013, which claims the benefit of Korean Patent Application No. 10-2012-0015545, filed on Feb. 15, 2012 and Korean Patent Application No. 10-2013-0016378, filed on Feb. 15, 2013, in the Korean Intellectual Property Office, the disclosures of all of which are incorporated herein by reference.

BACKGROUND

1. Field

Embodiments of the present invention relate to an X-ray device to acquire an image of an object for disease diagnosis.

2. Description of the Related Art

Clinical diagnosis has an important role in treatment of patients in medical operations, development of medical techniques greatly contributes to accurate clinical diagnosis and dependence thereon will continue to increase.

Accordingly, image diagnosis devices such as computer tomography (CT), magnetic resonance imaging (MRI) and X-ray devices have become essential in modern medical practice.

Generally, patients may feel fear or anxiety during an imaging operation performed using image diagnosis devices. Typically, patients are not aware when an imaging process is being performed or when it is completed, thus increasing fear or anxiety with regard to imaging diagnosis process.

SUMMARY

Therefore, it is one aspect of the present invention to provide an X-ray device to inform an object (e.g., medical patient) of X-ray irradiation through a sound and a method for controlling the same.

Additional aspects of the invention will be set forth in part in the description which follows and, in part, will be obvious from the description, or may be learned by practice of the invention.

In accordance with one aspect of the present invention, an X-ray device includes: an input portion to output a first-step press signal and a second-step press signal; a high-voltage generating portion to perform pre-heating, and to output a ready completion signal when the high-voltage generating portion completes pre-heating; a control portion to output a sound output signal when it receives both the second-step press signal output from the input portion and the ready completion signal output from the high-voltage generating portion; and a sound output portion to receive the sound output signal output from the control portion and to output a predetermined sound.

A time duration of the sound output by the source output portion is greater than a time duration of the high-voltage generating portion applying high voltage energy to an X-ray source.

The control portion outputs the sound output signal to the sound output portion, after it receives both the second-step press signal and the ready completion signal.

The input portion outputs the second-step press signal to at least one of the high-voltage generating portion and the control portion after it outputs the first-step press signal.

The input portion outputs the second-step press signal to at least one of the high-voltage generating portion and the control portion, after the ready completion signal is output from the high-voltage generating portion.

The X-ray device may further include an X-ray source; a detecting portion to detect an X-ray transmitted by the X-ray source, wherein the high-voltage generating portion outputs the first-step press signal to the detecting portion to enable the detecting portion to prepare for X-ray detection, when the high-voltage generating portion receives the first-step press signal from the input portion.

The detecting portion outputs a preparation completion signal, when it receives the first-step press signal output from the high-voltage generating portion and completes preparation for X-ray detection, and the high-voltage generating portion outputs a ready completion signal to the control portion, when it receives the preparation completion signal output from the detecting portion and completes pre-heating.

The high-voltage generating portion receives the second-step press signal output from the input portion, generates a high voltage and applies the same to an X-ray source.

The sound output portion outputs a sound comprising a camera shutter sound, when it receives the sound output signal.

In accordance with another aspect of the present invention, an X-ray device includes: an input portion to receive a user input; a high-voltage generating portion to output a ready completion signal, when the high-voltage generating portion completes pre-heating; a detecting portion to prepare for X-ray detection, and to output a preparation completion signal, when it completes X-ray detection preparation; a control portion to output a sound output signal, when it receives the ready completion signal output from the high-voltage generating portion and the preparation completion signal output from the detecting portion; and a sound output portion to receive the sound output signal output from the control portion and to output a predetermined sound.

A time duration of the sound output by the source output portion is greater than a time duration of the high-voltage generating portion applying high voltage energy to an X-ray source.

The input portion is configured to output a first-step press signal and a second-step press signal, and the control portion outputs the sound output signal to the sound output portion, after it receives all of the second-step press signal, the ready completion signal output from the high-voltage generating portion and the preparation completion signal output from the detecting portion.

The input portion is configured to output a first-step press signal and a second-step press signal, and the input portion outputs the second-step press signal to at least one of the high-voltage generating portion and the control portion, after it outputs the first-step press signal.

The input portion is configured to output a first-step press signal and a second-step press signal, and the input portion outputs the second-step press signal to at least one of the high-voltage generating portion and the control portion, after the preparation completion signal is output from the detecting portion or the ready completion signal is output from the high-voltage generating portion.

In accordance with another aspect of the present invention, a method for controlling an X-ray device includes: receiving, by a control portion, an irradiation command signal output via an input portion; receiving, by the control portion, a ready completion signal output from a high-voltage generating portion; and outputting a sound output signal from the control portion to a sound output portion, when the control portion receives both the irradiation command signal and the ready completion signal.

The irradiation command signal comprises a second-step press signal output from the input portion.

The method further includes: generating high voltage energy by the high-voltage generating portion; and performing an X-ray irradiation operation by an X-ray source using high voltage energy generated by the high-voltage generating portion, wherein a time duration of the sound output by the source output portion is greater than a time duration of X-ray irradiation by the X-ray source.

The method further includes: outputting a first-step press signal from the input portion to the high-voltage generating portion; outputting the first-step press signal from the high-voltage generating portion to a detecting portion, when the high-voltage generating portion receives the first-step press signal; outputting a preparation completion signal from the detecting portion to the high-voltage generating portion, when the detecting portion receives the first-step press signal output from the high-voltage generating portion and completes X-ray detection preparation; and outputting a ready completion signal from the high-voltage generating portion to the control portion, when the high-voltage generating portion receives the preparation completion signal output from the detecting portion and completes pre-heating.

The method further includes: outputting a second-step press signal from the input portion to at least one of the high-voltage generating portion and the control portion, after it outputs the first-step press signal to the high-voltage generating portion.

The method further includes: outputting the second-step press signal from the input portion to at least one of the high-voltage generating portion and the control portion, after the ready completion signal is output from the high-voltage generating portion.

The method further includes: outputting a sound output signal from the control portion to the sound output portion at a later time between a reception time of the second-step press signal and a reception time of the ready completion signal.

The method further includes: outputting the sound output signal from the control portion to the sound output portion, after the control portion receives both the second-step press signal and the ready completion signal.

In accordance with a further aspect of the present invention, a method for controlling an X-ray device includes: receiving, by a control portion, a second-step press signal output from an input portion, a ready completion signal output from a high-voltage generating portion and a preparation completion signal output from a detecting portion; and outputting a sound output signal from the control portion to a sound output portion, when the control portion receives the second-step press signal, the ready completion signal output from the high-voltage generating portion and the preparation completion signal output from the detecting portion.

The method further includes: outputting a first-step press signal from the input portion to the high-voltage generating portion; outputting the first-step press signal from the high-voltage generating portion to the detecting portion, when the high-voltage generating portion receives the first-step press signal; preparing for X-ray detection in the detecting portion, when the detecting portion receives the first-step press signal output from the high-voltage generating portion; and outputting the preparation completion signal from the detecting portion to the control portion, when the detecting portion completes X-ray detection preparation.

The method further includes: outputting the first-step press signal from the input portion to the high-voltage generating portion; preparing for X-ray detection in the high-voltage generating portion, when the high-voltage generating portion receives the first-step press signal; and outputting a ready completion signal from the high-voltage generating portion to the control portion, when the high-voltage generating portion completes pre-heating.

The method further includes: outputting the second-step press signal from the input portion to at least one of the high-voltage generating portion and the control portion, after the first-step press signal is output to the high-voltage generating portion.

The method further includes: outputting the second-step press signal from the input portion to at least one of the high-voltage generating portion and the control portion, after the ready completion signal is output from the high-voltage generating portion or the preparation completion signal is output from the detecting portion.

The method further includes: outputting the sound output signal from the control portion to the sound output portion at the latest time among reception times of the second-step press signal, the ready completion signal output from the high-voltage generating portion and the preparation completion signal output from the detecting portion.

The method further includes: outputting the sound output signal from the control portion to the sound output portion, after the control portion receives all of the second-step press signal, the ready completion signal output from the high-voltage generating portion and the preparation completion signal output from the detecting portion.

In accordance with the aspect of the present invention, a patient confirms an X-ray irradiation time through a sound, thus reducing fear or anxiety and imparting more convenient work environment for an operator.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Hereinafter, embodiments of the present invention will be described with reference to the accompanying drawings.

Figure 1:
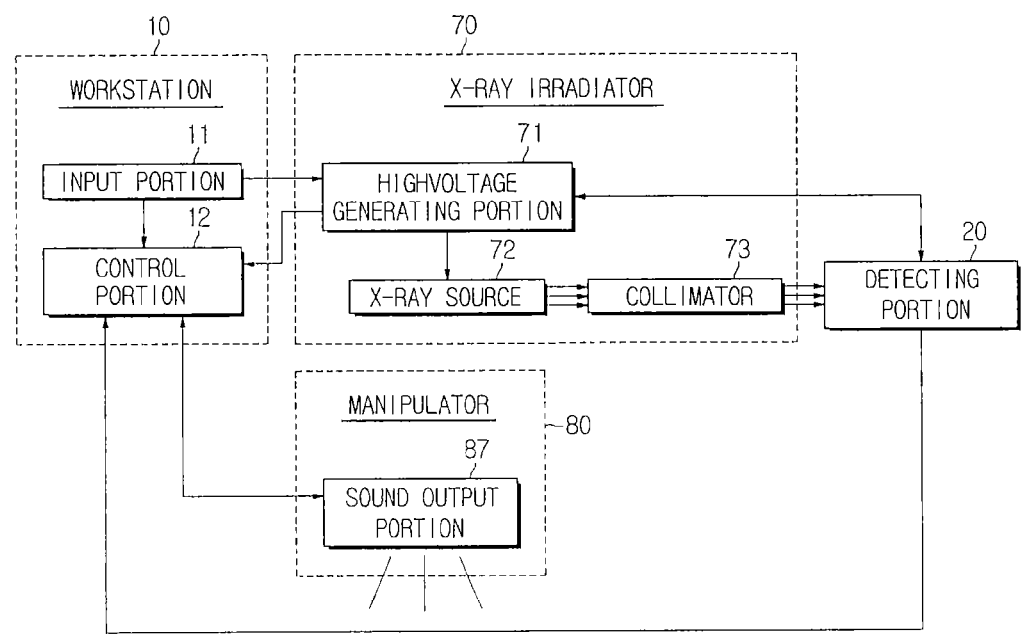
FIG. 1 is a block diagram illustrating a configuration of an X-ray device according to one embodiment of the present invention.
Figure 2:
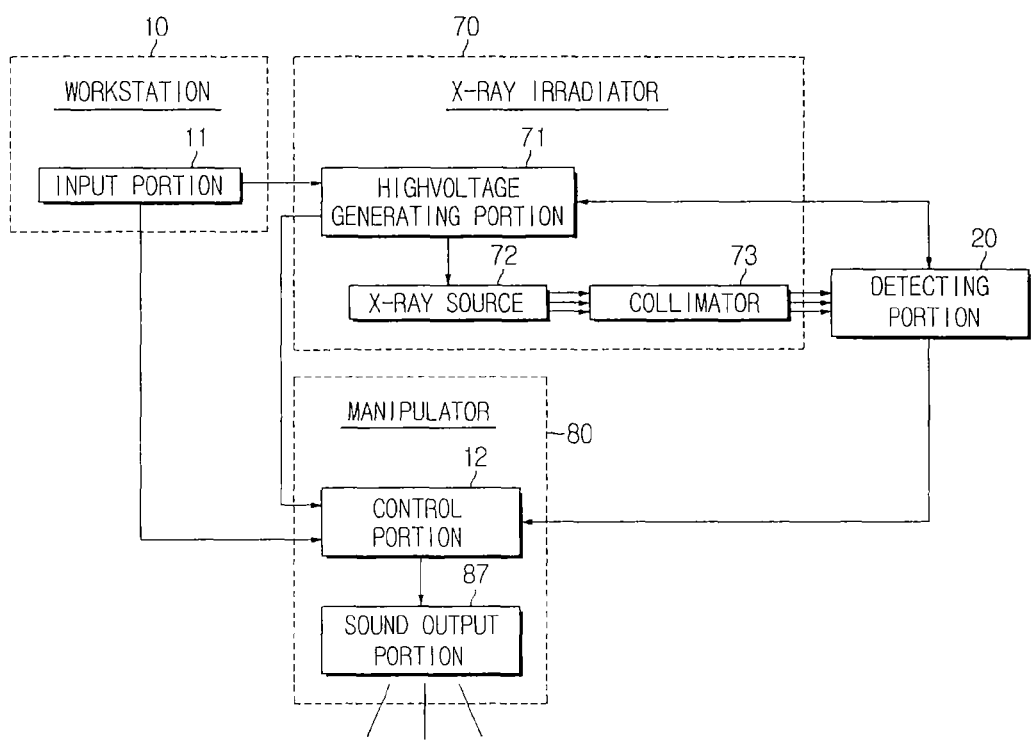
FIG. 2 is a block diagram illustrating a configuration of an X-ray device according to another embodiment of the present invention.
Figure 3:
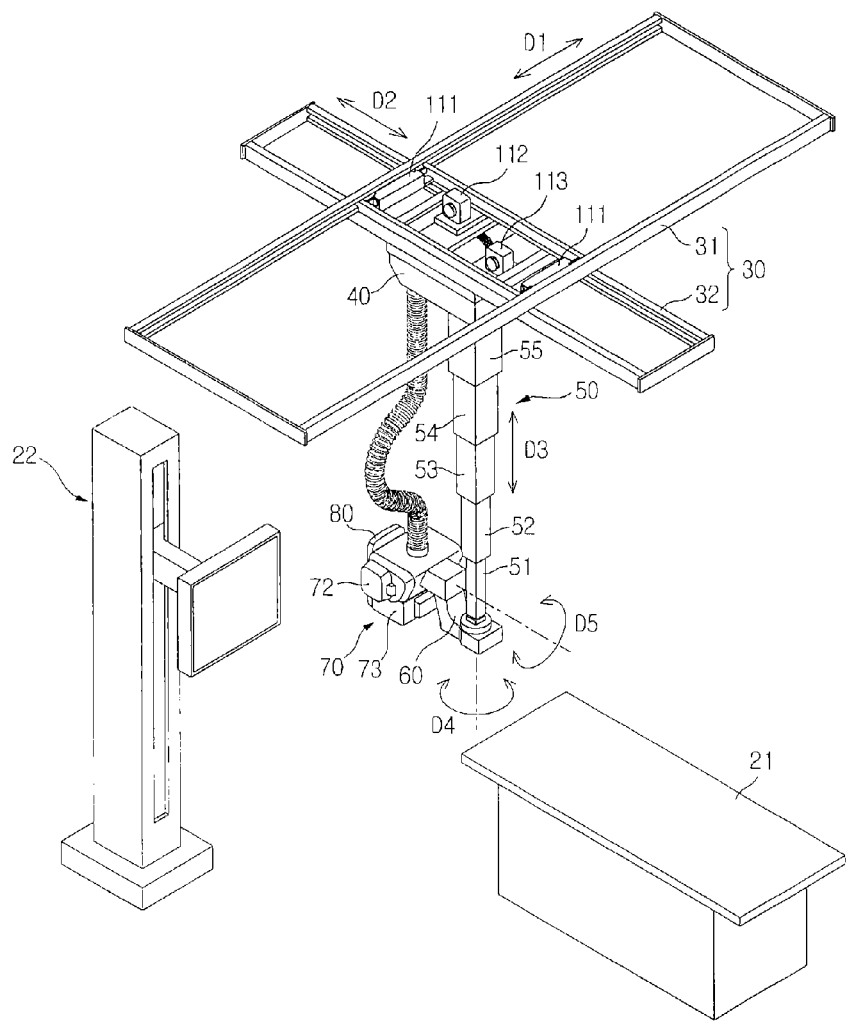
FIG. 3 is a perspective view illustrating the X-ray device of the embodiments of the present invention.
Figure 4:
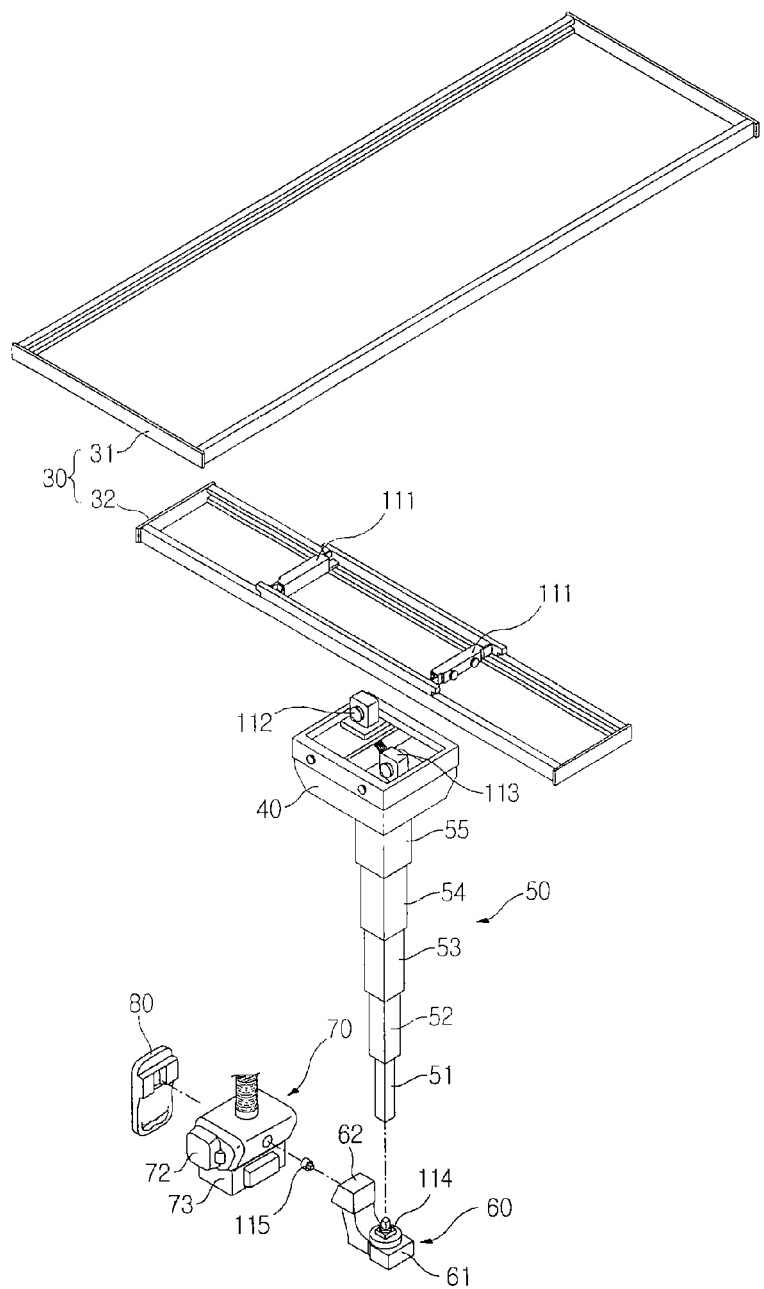
FIG. 4 is an exploded perspective view illustrating the X-ray device shown in FIG. 3.
Figure 5:
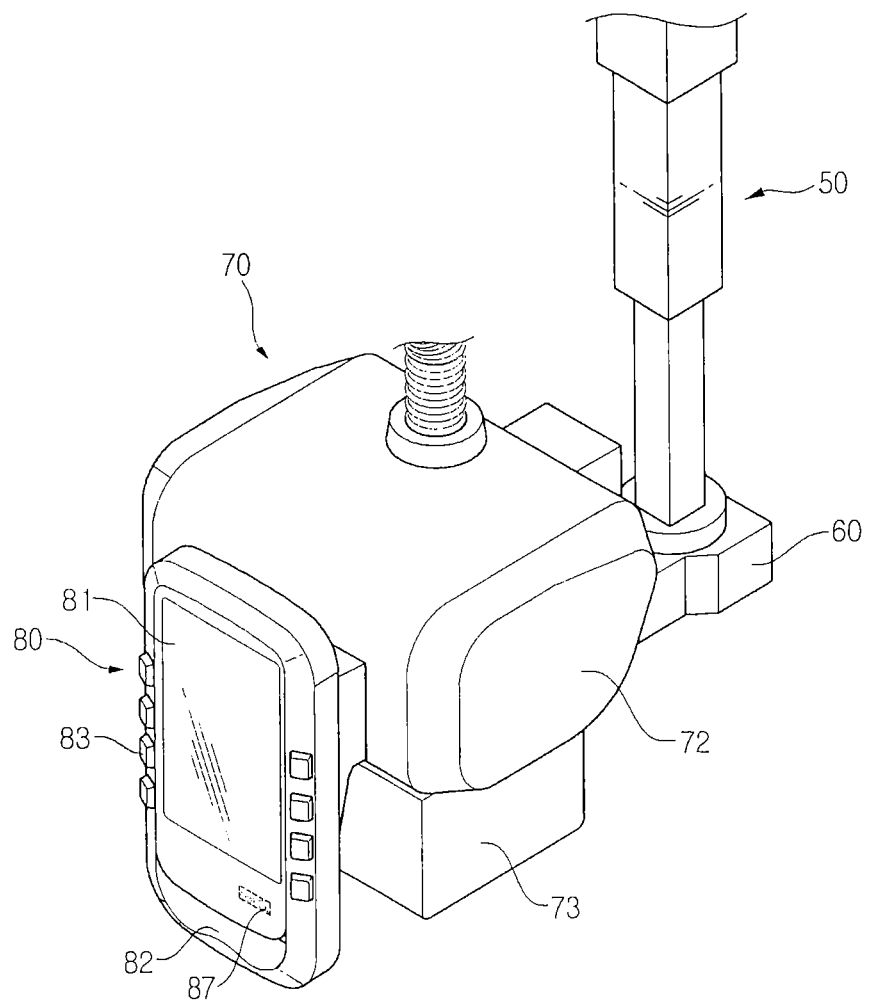
FIG. 5 is a perspective view illustrating a manipulator and an X-ray irradiator of the X-ray device shown in FIG. 3.

FIG. 1 is a block diagram illustrating a configuration of an X-ray device according to one embodiment of the present invention and FIG. 2 is a block diagram illustrating a configuration of an X-ray device according to another embodiment of the present invention. FIG. 3 is a perspective view illustrating the X-ray device of the embodiments of the present invention, FIG. 4 is an exploded perspective view illustrating the X-ray device shown in FIG. 3, and FIG. 5 is a perspective view illustrating a manipulator 80 and an X-ray irradiator of the X-ray device shown in FIG. 3.

Figure 6:
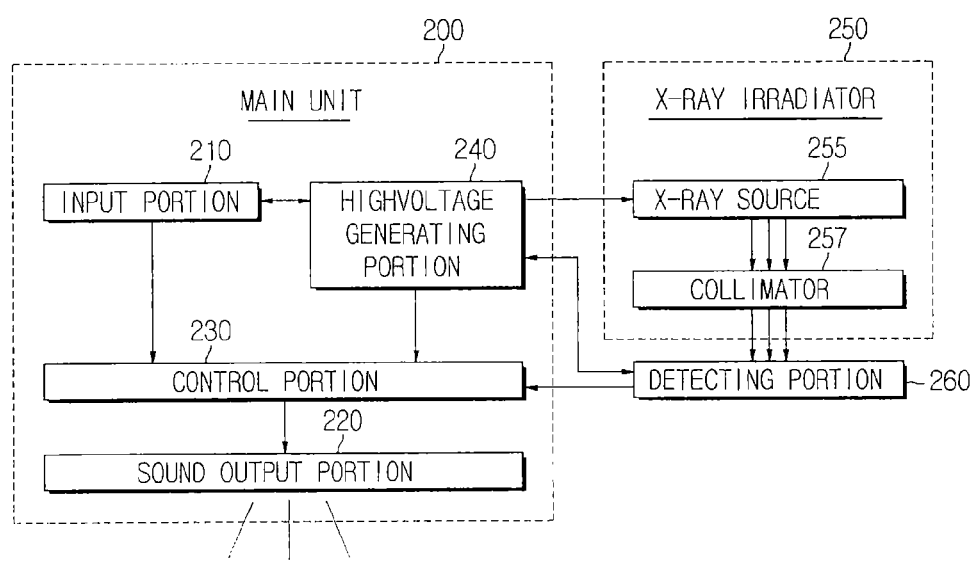
FIG. 6 is a block diagram illustrating a configuration of a mobile X-ray device according to another embodiment of the present invention.
Figure 7:
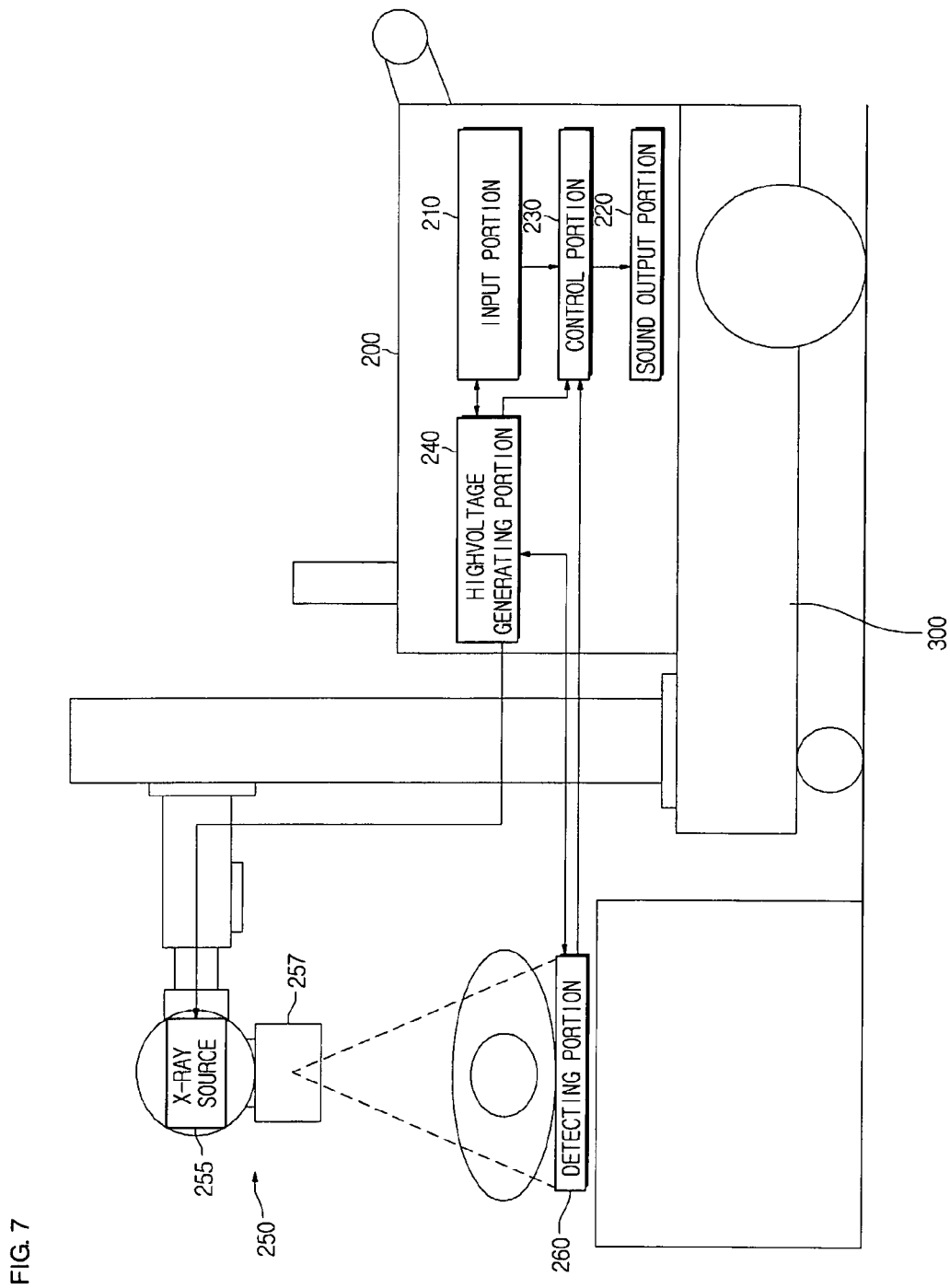
FIG. 7 is a concept view schematically illustrating the configuration of the mobile X-ray device of FIG. 6.

FIG. 6 is a block diagram illustrating a configuration of a mobile X-ray device according to another embodiment of the present invention and FIG. 7 is a concept view schematically illustrating the configuration of the mobile X-ray device of FIG. 6.

Referring to FIG. 1, the X-ray device according to one embodiment of the present invention includes: a workstation 10 including an input portion 11 to enable an operator to input a command to perform operation such as X-ray irradiation of the X-ray device and a control portion 12 to control the overall movement of the X-ray device; an X-ray irradiator 70 including a high-voltage generating portion 71 to generate a high voltage energy required for generation of an X-ray and apply the generated high voltage energy to an X-ray source 72, the X-ray source 72 to receive the high voltage energy generated by the high-voltage generating portion 71, and generate and irradiate an X-ray, and a collimator 73 to guide a passage of the X-ray irradiated from the X-ray source 72; a detecting portion 20 to detect the X-ray irradiated from the X-ray irradiator 70 and transmitted to an object; and a manipulator 80 including a sound output portion 87 to output an audio feedback sound such as camera shutter sound when an X-ray is irradiated under control of the control portion 12.

The operator inputs a command for X-ray irradiation through the input portion 11 and the input portion 11 may be provided with a two-step switch to input the command. The two-step switch may be provided to input an irradiation command for X-ray irradiation via a first-step press input and a second-step press input.

That is, a preparation command to instruct pre-heating for X-ray irradiation is input through the switch, when the operator presses the switch to the first-step press state, and an irradiation command for substantial X-ray irradiation is input through the switch, when the operator more deeply presses the switch to the second-step press state. As such, when the operator manipulates the switch, the input portion 11 produces signals, i.e., a first-step press signal and a second-step press signal, corresponding to the commands input through switch manipulation, and outputs the same to the high-voltage generating portion 71 to generate a high voltage for X-ray generation.

The high-voltage generating portion 71 receives the first-step press signal output from the input portion 11 and begins pre-heating, and outputs a ready completion signal to the control portion 12, when it completes pre-heating. In addition, the detecting portion 20 also requires X-ray detection preparation to perform X-ray detection. In this regard, the high-voltage generating portion 71 performs pre-heating and, at the same time, outputs the first-step press signal to the detecting portion 20 in order to enable the detecting portion 20 to prepare for detection of the X-ray transmitted to the object, when it receives the first-step press signal output from the input portion 11. The detecting portion 20 prepares for X-ray detection, when it receives the first-step press signal, and outputs a preparation completion signal to the high-voltage generating portion 71 and the control portion 12, when it completes X-ray detection preparation.

When pre-heating of the high-voltage generating portion 71 and X-ray detection preparation of the detecting portion 20 are completed and a second-step press signal is output from the input portion 11, the high-voltage generating portion 71 generates a high voltage and applies the same to the X-ray source 72, and the X-ray source 72 irradiates an X-ray. The control portion 12 outputs a sound output signal to the sound output portion 87 and allows the sound output portion 87 to output a sound such as a camera shutter sound, in order to inform the patient that an X-ray irradiation operation is currently being performed. The control of sound output of the sound output portion 87 by the control portion 12 will be described later in more detail.

FIG. 2 is a block diagram illustrating a configuration of an X-ray device according to another embodiment of the present invention.

Referring to FIG. 2, the X-ray device according to the embodiment of the present invention includes: a workstation 10 including an input portion 11 to enable an operator to input an command to perform an operation such as X-ray irradiation of the X-ray device; an X-ray irradiator 70 including a high-voltage generating portion 71 to generate a high voltage required for X-ray generation and apply the same to an X-ray source 72, the X-ray source 72 to receive the high voltage generated by the high-voltage generating portion 71, and generate and irradiate an X-ray, and a collimator 73 to guide a passage of the X-ray irradiated from the X-ray source 72; a detecting portion 20 to detect the X-ray irradiated from the X-ray irradiator 70 and transmitted to an object; and a manipulator 80 including a control portion 12 to control the overall movement of the X-ray device and a sound output portion 87 to output a sound such as camera shutter sound when an X-ray is irradiated under control of the control portion 12.

Unlike the embodiment illustrated in FIG. 1, in the embodiment illustrated in FIG. 2, the control portion 12 is included in the manipulator 80, rather than the workstation 10. The remaining configuration is the same as in FIG. 1 and a detailed explanation thereof is replaced by the description associated with FIG. 1. Hereinafter, a more detailed exterior appearance and configuration of the X-ray device shown in FIGS. 1 and 2 will be described with reference to FIGS. 3 to 5.

As shown in FIGS. 3 and 4, the X-ray device includes: a manipulator 80 providing an interface for manipulation of the X-ray device and including a sound output portion 87 to output a sound during X-ray irradiation, an X-ray irradiator 70 to irradiate an X-ray to an object, a detecting portion 20 to detect the X-ray transmitted to the object, a motor to supply a driving force to move the X-ray irradiator 70, a guide rail 30 to move the X-ray irradiator 70 through driving force of the motor, a movement carriage 40 and a post frame 50.

The guide rail 30 includes a first guide rail 31 and a second guide rail 32 that are disposed to form a predetermined angle together with each other. The first guide rail 31 and the second guide rail 32 preferably extend in a vertical direction to each other.

The first guide rail 31 is mounted on the ceiling of an inspection room in which the X-ray device is disposed.

The second guide rail 32 is disposed in a lower part of the first guide rail 31 and is slidably mounted on the first guide rail 31. A roller (not shown) movable along the first guide rail 31 may be mounted on the first guide rail 31. The second guide rail 32 connected to the roller (not shown) may be moved along the first guide rail 31.

A direction in which the first guide rail 31 extends is defined as a first direction D1 and a direction in which the second guide rail 32 extends is defined as a second direction D2. Accordingly, the first direction D1 and the second direction D2 are vertical to each other and are parallel to the ceiling of the inspection room.

The movement carriage 40 is disposed in a lower part of the second guide rail 32 such that it is movable along the second guide rail 32. A roller (not shown) movable along the second guide rail 32 may be mounted on the movement carriage 40.

Accordingly, the movement carriage 40 may be moved in the first direction D1 along the second guide rail 32 and in the second direction D2 along the second guide rail 32.

The post frame 50 is fixed on the movement carriage 40 and is disposed in a lower part of the movement carriage 40. The post frame 50 may be provided with a plurality of posts 51, 52, 53, 54 and 55.

The posts 51, 52, 53, 54 and 55 are foldably connected to one another, and lengths of the posts may increase or decrease in a vertical direction of the inspection room, while the post frame 50 is fixed on the movement carriage 40.

A direction in which the length of the post frame 50 increases or decreases is defined as a third direction D3. Accordingly, the third direction D3 may be vertical to the first direction D1 and the second direction D2.

The X-ray irradiator 70 may further include an X-ray source 72 to generate an X-ray, and a collimator 73 to control an irradiation region where an X-ray is generated and irradiated by the X-ray source 72. In addition, the X-ray irradiator 70 may further include a high-voltage generating portion 71 to apply a high voltage to the X-ray source 72.

The X-ray source 72 includes an X-ray tube and the X-ray tube may be realized with a double-electrode vacuum tube including an anode and a cathode. The X-ray tube is charged with a high vacuum of about 10 mmHg and a filament of the cathode is heated at a high temperature to generate thermions. The filament may be a tungsten filament and the filament may be heated by applying a voltage of 10V and a current of about 3 to 5 A to an electric wire connected to the filament.

In addition, when a high voltage of about 10 to 300 kvp is applied between the cathode and the anode, thermions are accelerated and collide with a target material of the anode to generate an X-ray. The generated X-ray is irradiated to the outside through a window and a beryllium thin film may be used as a material forming the window. In this case, most of energy of electrons colliding with the target material is converted into heat and the remainder is converted into X-rays.

The anode is generally composed of a copper, a target material is disposed in a side facing the cathode, and the target material may be a high resistance material such as Cr, Fe, Co, Ni, W or Mo. The target material is rotated by a rotating field when the target material is rotated and this fixing case exhibits an increased electron impact area and a 10-fold or more higher heat buildup ratio than in a fixed case.

A voltage applied to the cathode and the anode of the X-ray tube is referred to as a tube voltage, the tube voltage is applied from the high-voltage generating portion 71 and an intensity thereof is represented in kilovolt peak (kvp). When the tube voltage increases, a speed of thermions increases and, as a result, X-ray energy (energy of photons) generated by collision with the target material increases. A current flowing in the X-ray tube is referred to as a tube current and is represented in mA in average, and when the tube current increases, the number of thermions emitted from the filament increases and, as a result, an X-ray dose (the number of X-ray photons) generated by collision with the target material increases.

Accordingly, the energy of X-ray may be controlled by the tube voltage and the intensity or dose of X-ray may be controlled by tube current and X-ray exposure time.

The high-voltage generating portion 71 may be provided in the X-ray source 72, but the embodiment of the present invention is not limited thereto and may be provided in other regions of the X-ray device.

The detecting portion 20 detects the X-ray transmitted to the object using a digital detecting portion and may be realized as a table type 21 or a stand type 22. The detecting portion 20 may be realized using TFT or CCD.

A rotation joint 60 is disposed between the X-ray irradiator 70 and the post frame 50.

The rotation joint 60 couples the X-ray irradiator 70 to the post frame 50 and supports a load applied to the X-ray irradiator 70.

The rotation joint 60 may include a first rotation joint 61 connected to a lower post 51 of the post frame 50 and a second rotation joint 62 connected to the X-ray irradiator 70.

The first rotation joint 61 is rotatably provided based on a central axis of the post frame 50 extending in a vertical direction of the inspection room. Accordingly, the first rotation joint 61 may be rotated on the plane vertical to the third direction D3. In this case, a rotation direction of the first rotation joint 61 is newly defined as a fourth direction D4 which is a rotation direction of an axis parallel to the third direction D3.

The second rotation joint 62 is rotatably provided on the plane vertical to the ceiling of the inspection room. Accordingly, the second rotation joint 62 may rotate in a rotation direction of the axis parallel to the first direction D1 or the second direction D2. In this case, the second rotation joint 62 is newly defined as a fifth direction D5 which is a rotation direction of an axis extending in the first direction or the second direction.

The X-ray irradiator 70 is connected to the rotation joint 60 and is rotatably moved in the fourth direction D4 and the fifth direction D5. In addition, the X-ray irradiator 70 is connected to the post frame 50 through the rotation joint 60 and is linearly moved in the first direction D1, the second direction D2 and the third direction D3.

The X-ray irradiator 70 may be provided with a motor to enable movement in the first direction D1 to the fifth direction D5. The motor may be an electric motor and include an encoder.

The motor may include first, second, third, fourth and fifth motors 111, 112, 113, 114 and 115 in respective directions.

The respective motors 111, 112, 113, 114 and 115 may be disposed in various positions while taking into consideration ease of design. For example, the first motor 111 moving the second guide rail 32 in the first direction D1 is disposed near the first guide rail 31, the second motor 112 moving the movement carriage 40 in the second direction is disposed near the second guide rail 32, and the third motor 113 increasing or decreasing a length of the post frame 50 in the third direction D3 may be disposed in the movement carriage 40. In addition, the fourth motor 114 moving the X-ray irradiator 70 in the fourth direction D4 is disposed near the first rotation joint 61 and the fifth motor 115 rotatably moving the X-ray irradiator 70 in the fifth direction D5 is disposed near the second rotation joint 62.

Each motor 110 may be connected to a driving force transfer device (not shown) to linearly or rotatably move the X-ray irradiator 70 in the first direction D1 to the fifth direction D5. The driving force transfer device (not shown) may be a belt and pulley, chain and sprocket, shaft or the like.

The X-ray irradiator 70 is provided at one side thereof with a manipulator 80 to provide an interface to input a variety of information associated with X-ray imaging and manipulate a variety of devices.

As shown in FIG. 5, the manipulator 80 may be provided with a display portion 81 to provide an interface to input a variety of information associated with X-ray imaging and manipulate a variety of devices, a gripper 82 to enable the operator to grip and a button 83 to enable manipulation of the device. In addition, the manipulator 80 includes a sound output portion 87 to output a sound such as camera shutter sound upon X-ray irradiation in order to inform an object of completion of X-ray irradiation. In case of the X-ray device shown in FIG. 2, the control portion 12 to control movement of the sound output portion 87 is also included in the manipulator 80. Like the embodiment shown in FIG. 1, the control portion 12 may be provided in the workstation 10 to control movement of the sound output portion 87.

Although the X-ray device capable of performing the X-ray imaging is illustrated in FIGS. 1 to 5, a mobile X-ray device capable of performing X-ray imaging regardless of an imaging site is illustrated in FIGS. 6 and 7.

The mobile X-ray device illustrated in FIGS. 6 and 7 includes: a movement portion 300 provided with a wheel to move the X-ray device; a main portion 200 including an input portion 210 to input a command for manipulation of the X-ray device, a high-voltage generating portion 240 to generate a high voltage applied to the X-ray source 255, a sound output portion 220 to output a sound such as camera shutter sound when an X-ray is irradiated, and a control portion 230 to control the overall movement of the X-ray device; an X-ray irradiator 250 including an X-ray source 255 to generate an X-ray and a collimator 257 to guide a passage of the X-ray irradiated from the X-ray source 72; and a detecting portion 260 to detect the X-ray irradiated from the X-ray irradiator 70 and transmitted to an object.

An operator inputs a command for X-ray irradiation through the input portion 210 and the input portion 210 may be provided with a switch to input the command. The switch may be provided to input a command for X-ray irradiation when pressed twice.

That is, a preparation command to instruct pre-heating for X-ray irradiation is input through the switch, when the operator presses the switch, and a command for substantial X-ray irradiation is input through the switch, when the operator more deeply presses the switch in this state. When the operator manipulates the switch as described above, the input portion 11 produces signals, i.e., a first-step press signal and a second-step press signal, corresponding to the commands input through switch manipulation and outputs the same to the high-voltage generating portion 71 to generate a high voltage for X-ray generation.

The high-voltage generating portion 240 receives the first-step press signal output from the input portion 210 and begins pre-heating, and outputs a ready completion signal to the control portion 230, when completes pre-heating. In addition, the detecting portion 260 also requires X-ray detection preparation to perform X-ray detection. In this regard, the high-voltage generating portion 240 performs pre-heating and, at the same time, outputs a first-step press signal to the detecting portion 260 in order to enable the detecting portion 260 to prepare for detection of the X-ray transmitted to the object, when it receives the first-step press signal output from the input portion 210. The detecting portion 260 prepares for X-ray detection, when it receives the first-step press signal, and outputs a preparation completion signal to the high-voltage generating portion 240 and the control portion 230, when it completes X-ray detection preparation.

When pre-heating of the high-voltage generating portion 240 and X-ray detection preparation of the detecting portion 260 are completed and a second-step press signal is output from the input portion 210 to the high-voltage generating portion 240, the high-voltage generating portion 240 generates a high voltage and applies the same to the X-ray source 255, and the X-ray source 255 irradiates an X-ray. The control portion 230 outputs a sound output signal to the sound output portion 220 and allows the sound output portion 220 to output a sound such as a camera shutter sound, in order to inform the object of X-ray irradiation, when the second-step press signal is output from the input portion 11. The control of sound output of the sound output portion 87 by the control portion 12 will be described later in more detail.

Figure 8:
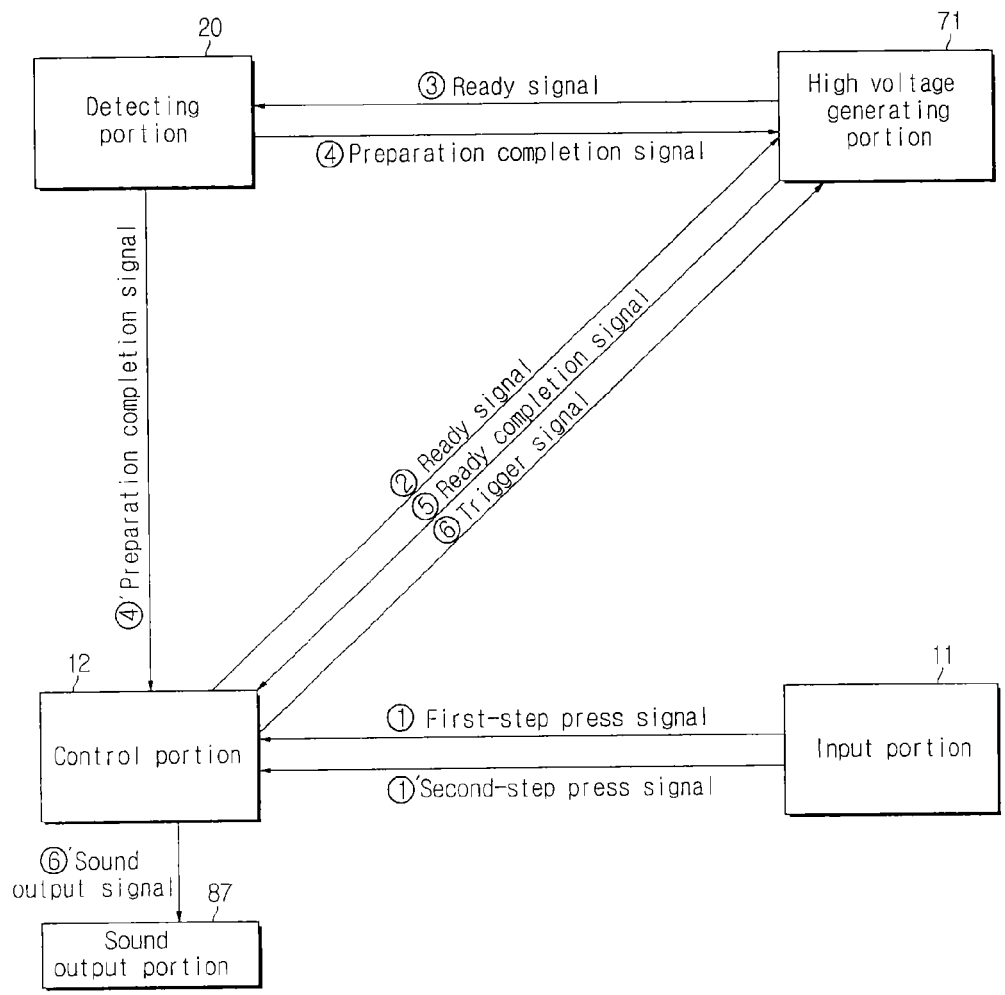
FIG. 8 is a diagram illustrating a process for controlling the X-ray device according to one embodiment of the present invention.
Figure 9:
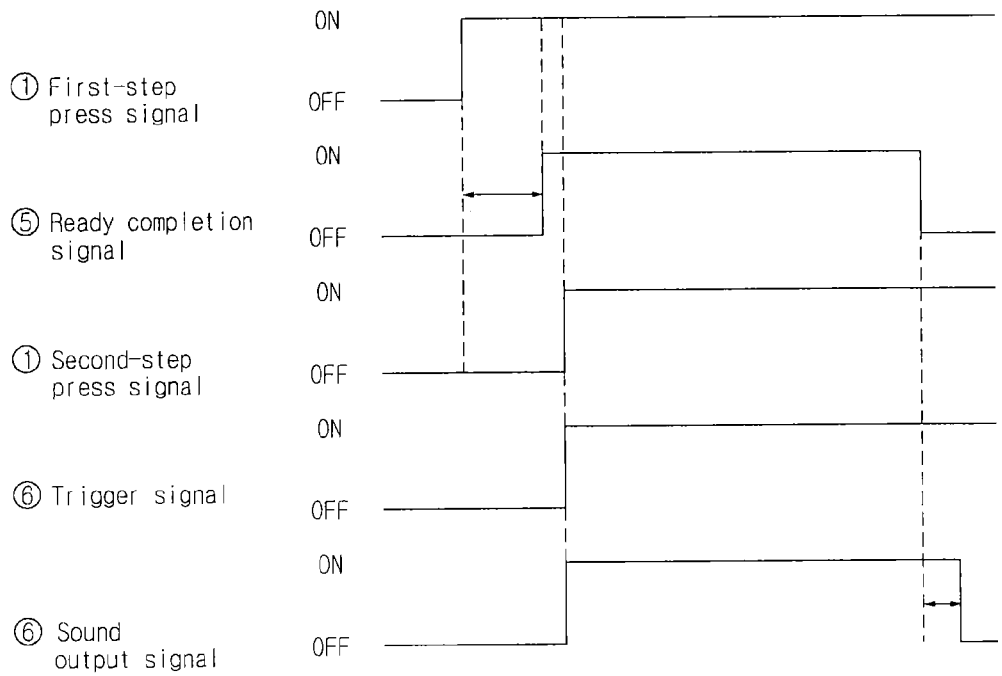
FIG. 9 is a timing chart illustrating an output order of respective signals during control process shown in FIG. 8 according to one embodiment of the present invention.

FIG. 8 is a view illustrating a process for controlling the X-ray device according to one embodiment of the present invention and FIG. 9 is a timing chart illustrating an output order of respective signals during the control process shown in FIG. 8.

As shown in FIG. 8, an input portion 11 outputs a first-step press signal (①) to the control portion 12. In response to receiving the first-step press signal (①), the control portion 12 transmits a ready signal (②) to the high-voltage generating portion 71 to instruct pre-heating of the high-voltage generating portion 71.

The high-voltage generating portion 71 begins pre-heating for generation of a high voltage when it receives the ready signal (②) from the control portion 12. Since a detecting portion 20 also requires X-ray detection preparation for X-ray detection, the high-voltage generating portion 71 begins pre-heating and outputs a ready signal (③) to the detecting portion 20 so that the detecting portion 20 can start preparing for X-ray detection, when it receives the ready signal (②) from the control portion 12. Alternatively, the ready signal (③) for starting the preparation process may be transmitted from the control portion 12 to the detecting portion 20.

The detecting portion 20 prepares for X-ray detection when it receives the ready signal (③) output from the high-voltage generating portion 71 or the control portion 12. The detecting portion 20 outputs a preparation completion signal (④) to the high-voltage generating portion 71 when it completes X-ray detection preparation. In addition, the detecting portion 20 outputs a preparation completion signal (④') to the control portion 12 in order to inform the control portion 12 that the detecting portion 20 has completed the preparation process.

The high-voltage generating portion 71 outputs a ready completion signal (⑤), indicating completion of preparation for X-ray irradiation, to the control portion 12 when it receives the preparation completion signal output from the detecting portion 20 and completes pre-heating. That is, the ready completion signal (⑤) output from the high-voltage generating portion 71 indicates completion of both X-ray detection preparation of the detecting portion 20 and pre-heating of the high-voltage generating portion 71.

The control portion 12 may inform the operator of completion of preparation for X-ray irradiation, and the operator inputs an X-ray irradiation command through the input portion 11 when the operator confirms completion of preparation for X-ray irradiation. The input portion 11 outputs a second-step press signal (①') to the control portion 12 when it receives the X-ray irradiation command from the operator. The control portion 12 outputs a trigger signal (⑥) to the high-voltage generating portion 71, which generates a high voltage energy, applies the same to the X-ray source 72 and thereby enables X-ray irradiation, when it receives the trigger signal (⑥) output from the control portion 12.

The control portion 12 outputs a sound output signal (⑥') to the sound output portion 87, when it receives the ready completion signal (⑤) from the high-voltage generating portion 71 and it transmits the trigger signal (⑥) to the high-voltage generating portion 71. The sound output portion 87 outputs a predetermined sound such as a camera shutter sound and informs an object of completion of X-ray irradiation when it receives the sound output signal output from the control portion 12. The camera shutter sound output from the sound output portion 87 is provided as an example and various types of effect sound or voice may be output.

In an embodiment, the control portion 12 is configured to output a sound output signal based on the second-step press signal output from the input portion 11.

More preferably, the control portion 12 outputs the sound output signal when it receives both the second-step press signal output from the input portion 11 and the ready completion signal output from the high-voltage generating portion 71. More specifically, the control portion 12 outputs the sound output signal at a later time among a reception time of the second-step press signal and a reception time of the ready completion signal. In a case in which the control portion 12 outputs the sound output signal as described above, the time at which a sound is output from the sound output portion 87 corresponds to an actual X-ray irradiation time as closely as possible. In the present embodiment, the control portion 12 outputs the sound output signal at the output time of the second-step press signal, since the second-step press signal is output after the ready completion signal is output. A case in which the time at which the second-step press signal is output is earlier than the time at which the ready completion signal is output will be described later with reference to FIGS. 10 and 11.

Referring to FIG. 9, the ready completion signal is output from the high-voltage generating portion 71 at a predetermined time after the first-step press signal is output from the input portion 11. The reason for this time gap is that it takes a given time for the detecting portion 20 to prepare for X-ray detection and for the high-voltage generating portion 71 to perform pre-heating. The time gap may be about 2 seconds or more.

The second-step press signal is output from the input portion 11 at a predetermined time after the ready completion signal is output from the high-voltage generating portion 71. The time gap may be determined depending on the time at which the X-ray irradiation command is input through the input portion 11.

The sound output signal is output at the time at which the second-step press signal is output from the input portion 11. The time at which the sound output signal is output may be later than the predetermined time at which the second-step press signal is output within a predetermined range. According to an aspect of an embodiment, a time duration of the sound (⑥') generated by the sound output portion 87 is greater than a time duration of high voltage energy applied to the X-ray source. Specifically, when an X-ray irradiation operation is completed, the ready completion signal output by the high-voltage generating portion 71 transitions from high to low, as seen by referring to FIG. 9, to indicate to the control portion 12 that the X-ray irradiation operation is terminated. As shown in FIG. 9, the control portion 12 is configured to turn off the sound generated by the sound output portion (as indicated, in FIG. 9, by the sound output signal (⑥') transitioning from high to low) only after it has received an indication from the high-voltage generating portion 71 that the X-ray irradiation operation is terminated (as indicated, in FIG. 9, by the ready completion signal (⑤) transitioning from high to low).

Figure 10:
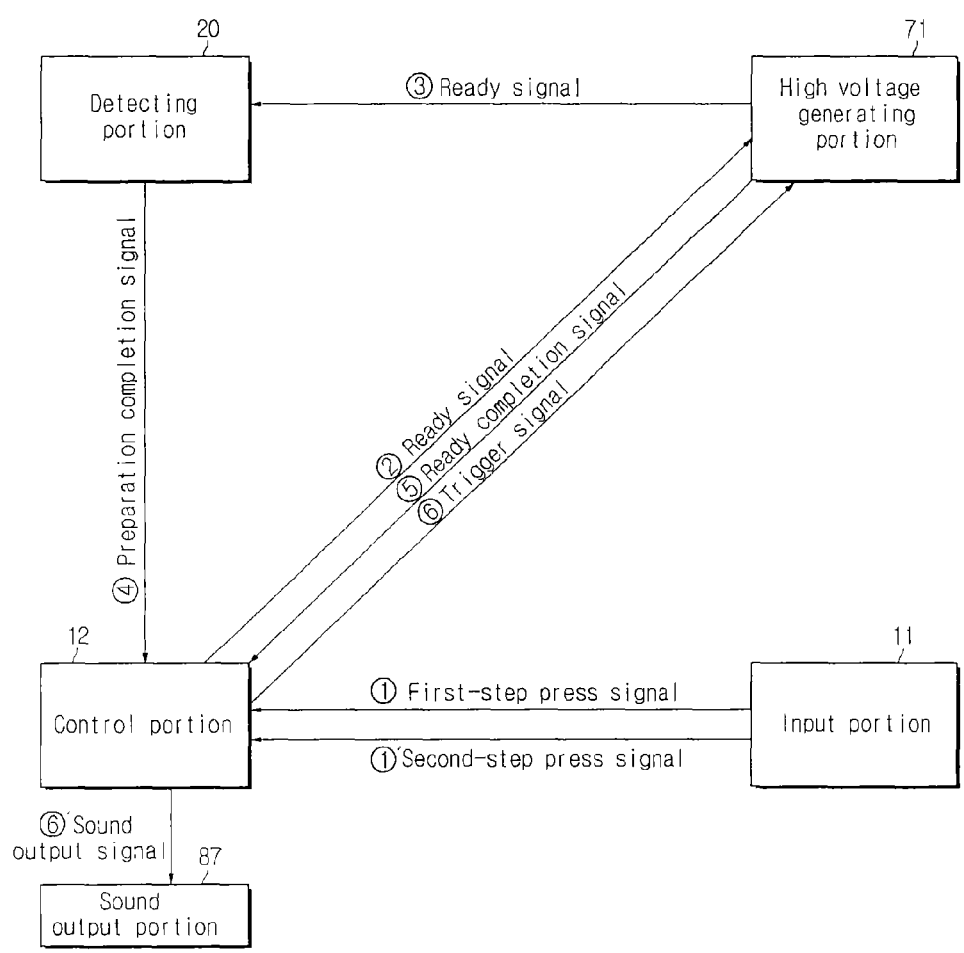
FIG. 10 is a diagram illustrating a process for controlling the X-ray device according to another embodiment of the present invention.
Figure 11:
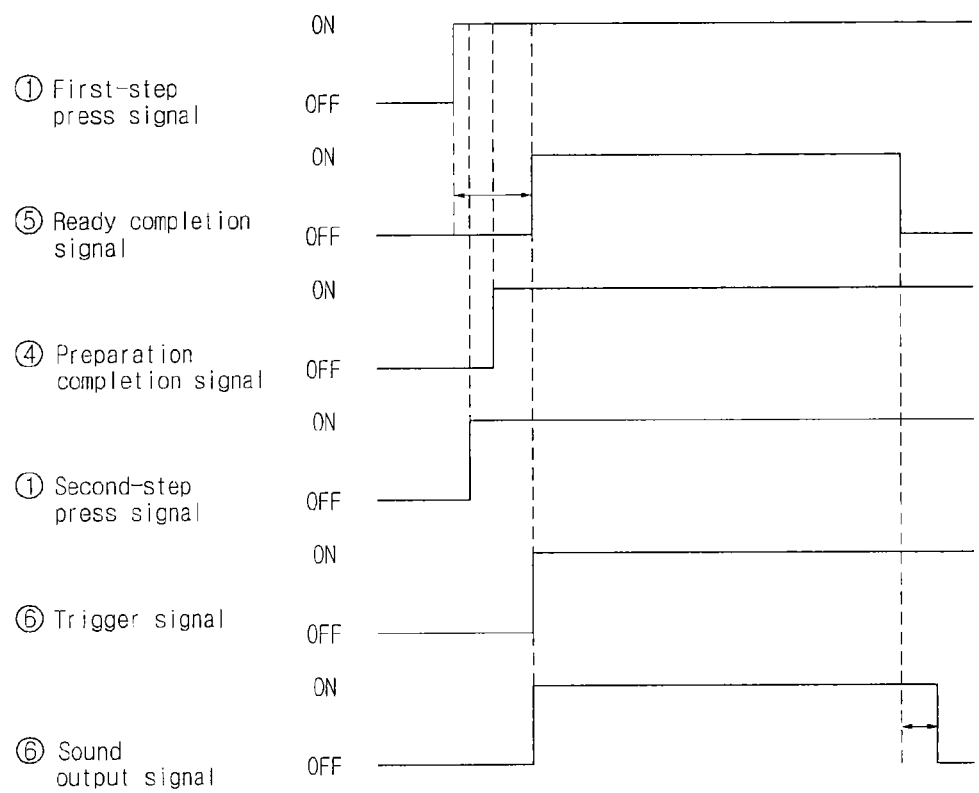
FIG. 11 is a timing chart illustrating an output order of respective signals during control process shown in FIG. 10 according to another embodiment of the present invention.

FIG. 10 is a view illustrating a process for controlling the X-ray device according to another embodiment of the present invention and FIG. 11 is a timing chart illustrating an output order of respective signals during the control process shown in FIG. 10.

As shown in FIG. 10, the input portion 11 outputs a first-step press signal (①) to the control portion 12. In response to receiving the first-step press signal (①), the control portion 12 transmits a ready signal (②) to the high-voltage generating portion 71 to instruct pre-heating of the high-voltage generating portion 71. In addition, the input portion 11 outputs a second-step press signal (e.g., irradiation command signal) thereto (①') to the control portion 12 in response to an irradiation command input by an operator.

Although an operator may input an X-ray irradiation command (second-step press input) through the input portion 11 after confirming completion of pre-heating of the high-voltage generating portion 71, FIGS. 10 and 11 illustrate the operator inputting the preparation command (first-step press input) and the X-ray irradiation command (second-step press input) without confirming completion of pre-heating of the high-voltage generating portion 71. As a result, the first-step press signal and the second-step press signal are output within a short time interval from the input portion 11 to the control portion 12. The second-step press signal is output after the first-step press signal is output due to the mechanical structure of the two-step switch provided in the input portion 11. When the second-step press signal is output from the input portion 11 as described above, the high-voltage generating portion 71 applies a high voltage to the X-ray source 72 immediately after completion of pre-heating in response to a trigger signal (⑥) from the control portion 12.

The high-voltage generating portion 71 begins pre-heating for generation of a high voltage when it receives the ready signal (②) from the control portion 12. Since the detecting portion 20 also requires detection preparation for X-ray detection, the high-voltage generating portion 71 begins pre-heating and outputs a ready signal (③) to the detecting portion 20 so that the detecting portion 20 can start preparing for X-ray detection, when it receives the ready signal (②) from the control portion 12. Alternatively, the ready signal (③) for starting the preparation process may be transmitted from the control portion 12 to the detecting portion 20.

The detecting portion 20 prepares for X-ray detection when it receives the ready signal (③) output from the high-voltage generating portion 71 or the control portion 12. The detecting portion 20 outputs a preparation completion signal (④) to control portion 12 when it completes X-ray detection preparation. The high-voltage generating portion 71 outputs a ready completion signal (⑤), indicating completion of preparation for X-ray irradiation, to the control portion 12 when it receives the preparation completion signal output from the detecting portion 20 and completes pre-heating. That is, the ready completion signal (⑤) output from the high-voltage generating portion 71 indicates completion of pre-heating of the high-voltage generating portion 71.

The control portion 12 outputs a sound output signal (⑥') to the sound output portion 87, when it receives the ready completion signal from the high-voltage generating portion 71 (⑤) and the preparation completion signal (④) from detecting portion 20. The sound output portion 87 outputs a predetermined sound such as a camera shutter sound and informs an object of completion of X-ray irradiation when it receives the sound output signal output from the control portion 12.

The control portion 12 outputs the sound output signal when it receives both the second-step press signal output from the input portion 11, the ready completion signal output from the high-voltage generating portion 71 and the preparation completion signal (④) from detecting portion 20. More specifically, the control portion 12 outputs the sound output signal at the later time among a reception time of the second-step press signal, a reception time of the ready completion signal and preparation completion signal. In a case in which the control portion 12 outputs the sound output signal as described above, the time at which a sound is output from the sound output portion 87 corresponds to an actual X-ray irradiation time as closely as possible. In the present embodiment, unlike the description with reference to FIGS. 8 and 9, the control portion 12 outputs the sound output signal at the time at which the ready completion signal is output from the high-voltage generating portion 71, since the second-step press signal and the first-step press signal are substantially simultaneously output, that is, the second-step press signal is output earlier than the ready completion signal.

Referring to FIG. 11, the ready completion signal is output from the high-voltage generating portion 71 at a predetermined time after the first-step press signal is output from the input portion 11. The reason for this time gap is that it takes a given time for the detecting portion 20 to prepare for X-ray detection and for the high-voltage generating portion 71 to perform pre-heating. The time gap may be about 2 seconds or more.

As described above, the second-step press signal is output a short time after the first-step press signal is output.

The sound output signal is output at the time at which the ready completion signal is output from the high-voltage generating portion 71. The time at which the sound output signal is output may be later than the predetermined time at which the ready completion signal is output, within a predetermined range.

Figure 12:
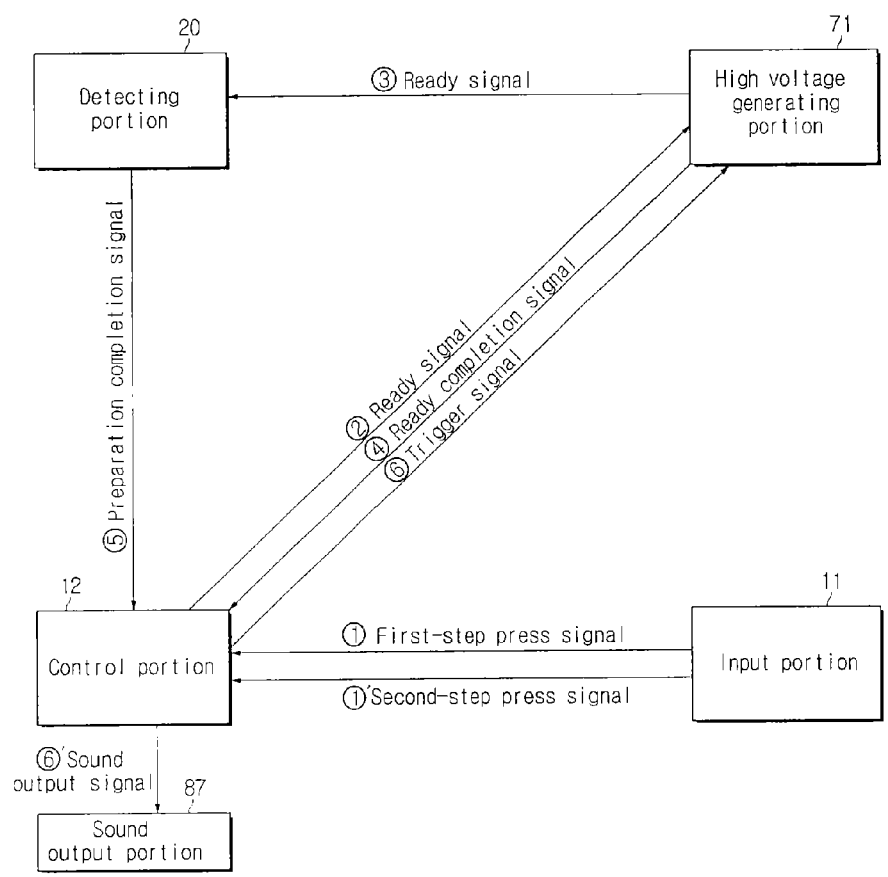
FIG. 12 is a diagram illustrating a process for controlling the X-ray device according to another embodiment of the present invention.
Figure 13:
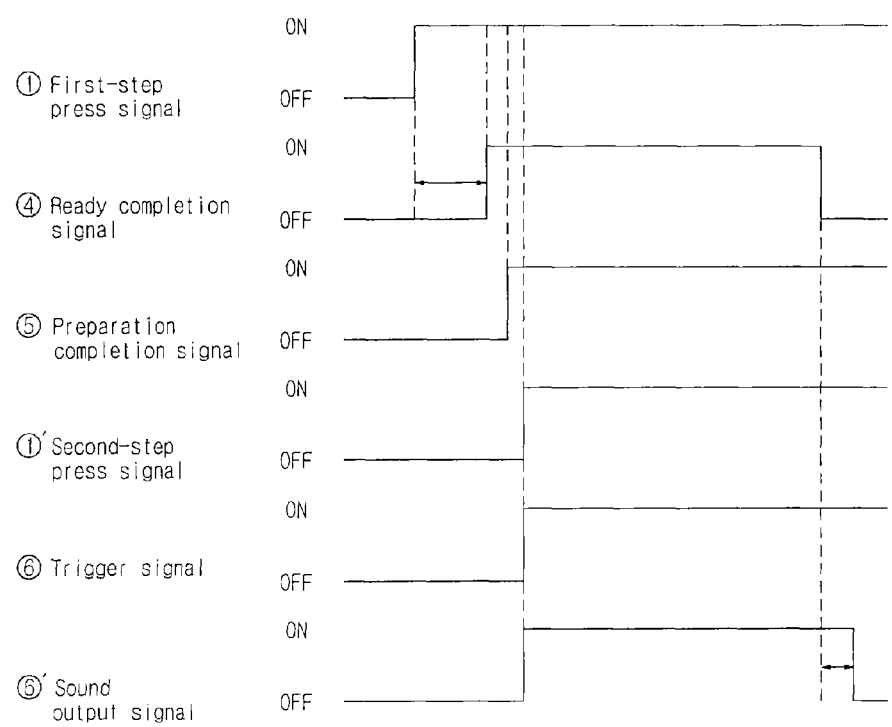
FIG. 13 is a timing chart illustrating an output order of respective signals during control process shown in FIG. 12 according to another embodiment of the present invention.

FIG. 12 is a view illustrating a process for controlling the X-ray device according to another embodiment of the present invention and FIG. 13 is a timing chart illustrating an output order of respective signals during the control process shown in FIG. 12.

As shown in FIG. 12, the input portion 11 outputs a first-step press signal (①) to the control portion 12. In response to receiving the first-step press signal (①), the control portion 12 transmits a ready signal (②) to the high-voltage generating portion 71 to instruct pre-heating of the high-voltage generating portion 71. The high-voltage generating portion 71 begins pre-heating for generation of a high voltage when it receives the ready signal (②) from the control portion 12. Since the detecting portion 20 also requires detection preparation for X-ray detection, the high-voltage generating portion 71 begins pre-heating and outputs a ready signal (③) to the detecting portion 20 so that the detecting portion 20 can start preparing for X-ray detection, when it receives the ready signal (②) from thecontrol portion 12. Alternatively, the ready signal (③) for starting the preparation process may be transmitted from the control portion 12 to the detecting portion 20.

The detecting portion 20 prepares for X-ray detection when it receives the ready signal (③) output from the high-voltage generating portion 71 or the control portion 12. The detecting portion 20 outputs a preparation completion signal (⑤) to the high-voltage generating portion 71 when it completes X-ray detection preparation.

The high-voltage generating portion 71 outputs a ready completion signal (④), indicating completion of preparation for X-ray irradiation, to the control portion 12 when it completes pre-heating.

Unlike the embodiments described above, the detecting portion 20 outputs the preparation completion signal (⑤) to only the control portion 12, and the ready completion signal (④) output from the high-voltage generating portion 71 indicates only completion of pre-heating of the high-voltage generating portion 71 and does not indicate completion of X-ray detection preparation of the detecting portion 20. That is, the ready completion signal output from the high-voltage generating portion 71 and the preparation completion signal output from the detecting portion 20 indicate completion of pre-heating and completion of preparation for X-ray irradiation. The preparation completion signal may be output earlier than the ready completion signal (FIG. 13), or the ready completion signal may be output earlier than the preparation completion signal (FIG. 11). In the present embodiment, a case in which the preparation completion signal is output earlier than the ready completion signal is described with reference to FIGS. 12 and 13. A case in which the ready completion signal is output earlier than the preparation completion signal is described with reference to FIGS. 10 and 11.

The control portion 12 may inform the operator of completion of preparation for X-ray irradiation through a display portion or the like, when it receives both the preparation completion signal output from the detecting portion 20 and the ready completion signal output from the high-voltage generating portion 71, and the operator inputs an X-ray irradiation command (second-step press input) through the input portion 11 when the operator confirms completion of X-ray irradiation preparation. The input portion 11 outputs a second-step press signal (①') to the control portion 12 when it receives an X-ray irradiation command from the operator. The high-voltage generating portion 71 generates a high voltage, applies the same to the X-ray source 72 and thereby enables X-ray irradiation, when it receives the trigger signal (⑥) output from the control portion 12.

In an embodiment, the control portion 12 is configured to output the sound output signal when it receives the preparation completion signal from the detecting portion 20 and the second-step press signal output from the input portion 11.

More specifically, the control portion 12 outputs a sound output signal to the sound output portion 87, when it receives the preparation completion signal from the detecting portion 20, the ready completion signal from the high-voltage generating portion 71 and the second-step press signal from the input portion 11 (⑥). The sound output portion 87 outputs a predetermined sound such as a camera shutter sound and informs an object of completion of X-ray irradiation when it receives the sound output signal output from the control portion 12. The camera shutter sound output from the sound output portion 87 is provided as an example and various types of effect sound or voice may be output.

Referring to FIG. 13, at a predetermined time after the first-step press signal is output from the input portion 11, the preparation completion signal is output from the detecting portion 20 and the ready completion signal is output from the high-voltage generating portion 71. In the present embodiment, the preparation completion signal is output earlier than the ready completion signal.

The second-step press signal is output from the input portion 11 at a predetermined time after the ready completion signal is output from the high-voltage generating portion 71. The time gap may be determined depending on the time at which the X-ray irradiation command is input through the input portion 11.

The sound output signal is output at the time at which the second-step press signal is output from the input portion 11. The time at which the sound output signal is output may be later than the predetermined time at which the second-step press signal is output within a predetermined range.

As shown in FIG. 13, the sound output signal (⑥)' is output at the time at which the preparation completion signal (⑤) is output from the detecting portion 20. Alternatively, the time at which the sound output signal (⑥)' is output may be later than the predetermined time at which the preparation completion signal (⑤) is output within a predetermined range.

By controlling an activation of the sound output portion 87 through the afore-mentioned control process, it is possible to output a sound such as camera shutter sound at the time of X-ray irradiation and inform a patient of X-ray irradiation.

In addition, the control portion 12 may control the operation of the sound output portion 87 such that information related to the instructions required for a patient at each stage of the X-ray imaging or information related to the progress of imaging is output through the sound output portion 87 in the form of a sound.

For example, the control portion 12, at a stage before the X-ray imaging, that is, at a stage before the X-ray imaging starts, may control the sound output portion 87 to output 1) information related to a progress of the imaging indicating that the X-ray image is to be conducted soon, 2) information related to the total number of imaging operations when the X-ray image is achieved through a plurality of number of times of imaging operations, and 3) information related to instructions for an object instructing an object to place a desired region (for example, chest) on the X-ray device and hold breath without moving in the form of sound.

The sound output portion 87, according to the control by the control portion 12, converts the following details of examples into the form of a speech signal. For example, the sound output portion 87 outputs sound stating "X-ray imaging is to be conducted soon", "Three times of imaging operations are to be conducted consecutively", "Please place the chest part on the X-ray device and hold breath without moving", and "X-ray imaging begins" to notify a patient of the progress of X-ray imaging and instructions required.

In addition, the sound output portion 87, at a stage of performing the X-ray imaging by radiating X-rays at the object, may output information related to the progress of the X-ray imaging indicating that the image is achieved as X-rays are radiated.

For example, as described above, as the X-rays are radiated, the control portion 12 may control the sound output portion 87 such that a sound, such as a camera shutter sound, or a sound stating "X-rays are radiated" is output through the sound output nit 87.

In addition, when the X-ray imaging is achieved through a plurality of times of imaging operations, the control portion 12 may allow a camera shutter sound sounding "click" at each count of imaging operations or a sound stating "two rounds of imaging operations remain" and "one round of imaging operations remains" to be output through the sound output portion 87 such that the patient is notified of the number of imaging operations remaining.

In addition, the control portion 12, if the X-ray imaging is completed, may control the sound output portion 87 to output a voice stating "X-ray imaging is completed" and "Thank you" such that the patient is notified of the completion of the X-ray imaging.

The expressions or sound being output through the sound output portion 87 at each stage of the X-ray imaging are provided as an example. An operator may use different types of sounds or edit the expressions to output a desired sound.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:
1. A method of an X-ray device, comprising:
receiving an input which requests an X-ray irradiation, by a control portion;
receiving an X-ray irradiation ready signal which indicates that an X-ray irradiation is ready from an X-ray irradiator, by the control portion;
producing, by the control portion, a trigger signal to irradiate an X-ray when the input and the X-ray irradiation ready signal are received;
determining which of the X-ray irradiation ready signal and the input is received later; and
producing a sound signal at a time when the input is received or when the X-ray irradiation ready signal is received, whichever is received later determined based on the determining, the sound signal being controllable to output a sound to provide information about irradiation of the X-ray.

2. The method according to claim 1, wherein when the determining determines that the X-ray irradiation ready signal is received earlier than the input is received, the trigger signal is produced when the input is received, and the sound signal is produced just before the trigger signal is sent to the X-ray irradiator and continuously produced until just after the X-ray irradiation ready signal is turned off which indicates a termination of the X-ray irradiation.

3. The method according to claim 2, wherein the sound is produced in response to the sound signal to alert a patient when the X-ray irradiation is started and when the X-ray irradiation is completed.

4. The method according to claim 3, wherein the sound is produced by an X-ray source manipulator positioned adjacent to a patient position during the irradiation of the X-ray.

5. The method according to claim 4, wherein the sound comprises a camera shutter click sound.

6. The method according to claim 1, wherein when the determining determines that the X-ray irradiation ready signal is received later than the input is received, the trigger signal is produced when the X-ray irradiation ready signal is received, and the sound signal is produced just before the trigger signal is sent to the X-ray irradiator and continuously produced until just after the X-ray irradiation ready signal is turned off which indicates a termination of the X-ray irradiation.

7. An X-ray device, comprising:
an input portion to receive an operator command to perform an X-ray irradiation and to send an X-ray irradiation command signal based on the operator command;
a control portion
to receive an X-ray irradiation ready signal which indicates that an X-ray irradiation is ready from an X-ray irradiator,
to produce a trigger signal to irradiate an X-ray when the X-ray irradiation command signal and the X-ray irradiation ready signal are received, and
to determine which of the X-ray irradiation ready signal and the X-ray irradiation command signal is received later; and
a sound output portion to produce a sound signal at a time when the X-ray irradiation command signal is received or when the X-ray irradiation ready signal is received, whichever is received later determined by the control portion, the sound signal being controllable to output a sound to provide information about irradiation of the X-ray.

8. The X-ray device according to claim 7, wherein when the control portion determines that the X-ray irradiation ready signal is received earlier than the X-ray irradiation command signal is received, the trigger signal is produced when the operator command is received, and the sound signal is produced just before the trigger signal is sent to the X-ray irradiator and continuously produced until after the X-ray irradiation ready signal is turned off which indicates a termination of the X-ray irradiation.

9. The X-ray device according to claim 7, wherein when the control portion determines that the X-ray irradiation ready signal is received later than the X-ray irradiation command signal is received, the trigger signal is produced when the X-ray irradiation ready signal is received, and the sound signal is produced just before the trigger signal is sent to the X-ray irradiator and continuously produced until just after the X-ray irradiation ready signal is turned off which indicates a termination of the X-ray irradiation.

10. An X-ray device, comprising:
an input portion to receive an operator command to perform an X-ray irradiation and to produce an X-ray irradiation command signal in response to the received operator command;
an X-ray detecting portion to detect the X-ray irradiated from an X-ray source when the X-ray irradiation command signal is produced and to produce an X-ray detection preparation completion signal which indicates that the X-ray detecting portion is ready to detect the X-ray irradiated from the X-ray source; and
a control portion
to receive an X-ray irradiation ready signal which indicates that an X-ray irradiation is ready from an X-ray source,
to receive the X-ray detection preparation completion signal,
to produce a trigger signal to irradiate an X-ray when the X-ray irradiation ready signal and the X-ray detection preparation completion signal are received,
to determine which of the X-ray irradiation command signal, the X-ray detection preparation completion signal and the X-ray irradiation ready signal is received later, and
to produce a sound signal at a time when the X-ray irradiation command signal is received, or when the X-ray irradiation ready signal is received, or when the X-ray detection preparation completion signal is received, whichever is received later determined by the control portion, the sound signal being controllable to output a sound which provides information about stages of irradiation of the X-ray which is performed in response to the received irradiation command signal.

11. The X-ray device according to claim 10, further comprising a sound output portion to produce the sound in response to the sound signal received from the control portion.

12. The X-ray device according to claim 11, further comprising an X-ray source manipulator positioned adjacent to a patient position during the irradiation of the X-ray and comprising the sound output portion to output the sound.

13. The X-ray device according to claim 11, wherein the sound output portion produces a voice signal describing stages of the X-ray irradiation to a patient.

14. The X-ray device according to claim 10, wherein the sound signal is produced at a time an X-ray trigger signal is produced, the X-ray trigger signal being produced in response to the received irradiation command signal.

* * * * *

UNITED STATES PATENT AND TRADEMARK OFFICE
CERTIFICATE OF CORRECTION

PATENT NO. : 10,085,700 B2  
APPLICATION NO. : 14/269512  
DATED : October 2, 2018  
INVENTOR(S) : Hyun Sun Kim et al.

Page 1 of 1

It is certified that error appears in the above-identified patent and that said Letters Patent is hereby corrected as shown below:

On the Title Page

Item [30] (Foreign Application Priority Data), Line 2:
Below "10-2012-0015545" insert -- Feb 15, 2013 (KR) 10-2013-0016378 --.

Signed and Sealed this
Second Day of April, 2019

Andrei Iancu
*Director of the United States Patent and Trademark Office*